United States Patent [19]

Förster et al.

[11] 3,946,104

[45] Mar. 23, 1976

[54] METHOD OF PRODUCING AN HOMOGENEOUS GAS MIXTURE

[75] Inventors: Friedrich Förster, Dortmund-Wellinghofen; Erich Barth, Dortmund; Heinz-Jochen Keller, Dortmund-Horde, all of Germany

[73] Assignee: Friedrich Uhde GmbH, Dortmund, Germany

[22] Filed: July 8, 1974

[21] Appl. No.: 486,495

Related U.S. Application Data

[62] Division of Ser. No. 419,909, Nov. 29, 1973, Pat. No. 3,895,919.

[30] Foreign Application Priority Data

Jan. 13, 1973 Germany............................ 2301644

[52] U.S. Cl................................. 423/659; 423/359
[51] Int. Cl.$^2$........................ C01B 1/00; C01C 1/00
[58] Field of Search ........... 423/359, 360, 361, 659; 23/283, 288 R, 288 E, 289; 261/94, 95, 96, 102; 236/13

[56] References Cited

UNITED STATES PATENTS

| | | | |
|---|---|---|---|
| 2,632,692 | 3/1953 | Korin et al........................... | 423/361 |
| 3,442,626 | 5/1969 | Browne................................ | 423/361 |
| 3,598,541 | 8/1971 | Hennemuth et al.................. | 23/283 |
| 3,723,072 | 3/1973 | Carson et al........................ | 23/288 R |
| 3,787,189 | 1/1974 | Muffat et al......................... | 23/283 |

FOREIGN PATENTS OR APPLICATIONS 939,868      1956      Germany ........................... 423/359

*Primary Examiner*—Oscar R. Vertiz
*Assistant Examiner*—Eugene T. Wheelock
*Attorney, Agent, or Firm*—Malcolm W. Fraser

[57] ABSTRACT

A method for the production of a homogenous gas mixture from two gas streams of different parameters in which an open or free equalizing space downstream of a superimposed catalyst layer is provided. Within such open space is a mixing assembly imposing a little deflection upon the reaction gas stream causing a low pressure drop in the stream with a consequent reduced loss of energy. Quench gas is admitted through a two stage pressure reduction. It is first expanded from a duct surrounding the mixing assembly through a plurality of openings where the gas velocities are reduced and equalized. The second pressure reduction takes place across openings in the mixing assembly. Quench gas and reaction gas are then thoroughly mixed in the mixing assembly and the gas mixture is consequently passed to the entrance of a second catalyst layer downstream.

1 Claim, 2 Drawing Figures

METHOD OF PRODUCING AN HOMOGENEOUS GAS MIXTURE

This is a division of application Ser. No. 419,909 filed Nov. 29, 1973 now U.S. Pat. No. 3,895,919, issued July 22, 1975.

BACKGROUND OF THE INVENTION

The present invention relates to a device for the production of a homogenous gas mixture from two gas streams of different parameters, such as temperature, pressure, composition, flow velocity, etc., for multi-stage exothermic or endothermic reactions.

Devices of this type are preferably applied in ammonia and methanol synthesis facilities where reactions are performed in the presence of catalysts.

Such catalytic reactions require each reaction zone to receive a homogeneous gas mixture. A uniform gas temperature at the inlet to the catalyst layer is a prerequisite for a uniform reaction in the catalyst layer and, consequently, for a uniform utilization of and load on the catalyst. Otherwise, the catalyst volume in the reaction vessel would either not be utilized efficiently or would be overloaded with consequent damage to and inefficiency of the catalyst.

For complying with these requirement it is known to readjust, that means to cool or to heat, the incoming gas mixture from a preceding catalyst layer, hereinafter referred to as reaction gas stream A, by admixing unreacted gas of a lower or higher temperature level, hereinafter referred to as quench gas stream B, before the gas mixture composed of reaction gas stream A and quench gas stream B penetrates into the next catalyst layer.

In general, quench gas stream B is admixed to reaction gas stream A downstream of a restriction of the gas path cross section in the reaction vessel. This restriction which is followed by an enlarged cross section is intended to effect good mixing and, consequently, provide a uniform temperature of the gas stream over the entire cross-section area of the catalyst layer.

In general, quench gas stream B is only a fraction of reaction gas stream A and is admitted through a feed pipe into the space between two adjacent catalyst layers.

Referring to known process devices as described, for example, in U.S. Pat. No. 3,475,136 and German Pat. OS 289,847, the quench gas feed pipe terminates in a tubular ring or a multiarm tube distributor with a multitude of small lateral openings for discharging the quench gas into the free space. Referring to U.S. Pat. No. 3,475,136, the diameter of the free space is reduced to the diameter of the tubular ring at the point of quench gas admission. Referring to British Pat. No. 1,105,614, a device with rhombic cross-sectional area is placed into the single layer catalyst bed. This device essentially consists of a rugged wire mesh; it is substantially hollow and is provided with an annular shaped central quench gas distributor tube. The major portion of the reaction gas stream passes from the catalyst filled space into this free space where it undergoes a certain equalization of pressure differences and a mixing with the quench gas admitted.

Referring to known devices, said features may be summarized in that the reaction gas from the catalyst layer passes into what is called a free space, also called equalizing space. This space is provided with means, for example tubes or a multiarm tubular distributor, for combining the reaction gas with the gas to be admixed. Devices of known design have evidenced in practice, however, that the desired success is not achieved perfectly. It has regularly been found, for example, that there is a formation of gas streams which are not uniform, that means which are not of a steady temperature and composition. Consequently, the catalyst in the reactor is subject to different loads and is, therefore, not utilized uniformly or is exposed to local overheating with consequent premature damage to the catalyst.

SUMMARY OF THE INVENTION

The object of the present invention is to eliminate these deficiencies of the known devices and to obtain, with a minimum number of internals and with as little deflection as possible for the reaction gas stream, a completely homogeneous gas mixture at the inlet to and over the entire cross sectional area of the next catalyst layer.

According to this invention, the problem is solved by providing a free equalizing space downstream of a superimposed catalyst layer, a mixing assembly with upper and lower tube plates carrying mixing tubes with restriction orifice plates, said tubes being provided with lateral openings above the restriction orifice plates, a quench gas feed pipe terminating in an outer annular duct, the inner side wall of which is provided with openings, which are located at a level below the central restriction orifice plates.

The invention incorporates the particular advantage of a low pressure drop in the gas stream with consequent reduced loss of energy because only little deflection from its main direction of flow is imposed upon the reaction gas stream for its passage through the mixing tubes, which are uniformlly distributed over the cross sectional area of the reaction vessel. In addition, this arrangement prevents any repercussion on the passage of the gas stream across the catalyst layer above the mixing chamber. The uniform admission of quench gas is achieved through a two stage pressure reduction, the quench gas being first expanded from the annular duct through a multitude of openings into the space around the mixing tubes where the gas velocities are substantially reduced and equalized. Consequently, the pressure ahead of the openings in the mixing tubes is at the same level throughout. The second pressure reduction takes place across the openings of the mixing tubes with the quench gas being subjected to a strong increase in velocity. Quench gas and reaction gas are then thoroughly mixed through the restriction orifice plates arranged in the mixing tubes.

Admission of gas to the catalyst layer beneath the mixing chamber is uniform because the upstream cross sectional area of the gas flow was not reduced in its entirety, but was split up into a multitude of part stream restrictions. The mixing device has a moderate height as compared to known devices and mixing chambers. Appropriate mechanical design and the maintenance of close fabrication tolerances at the critical points of flow restriction and admission ensure good performance at part-load operation.

DESCRIPTION OF THE PREFERRED EMBODIMENT

Figure 1:
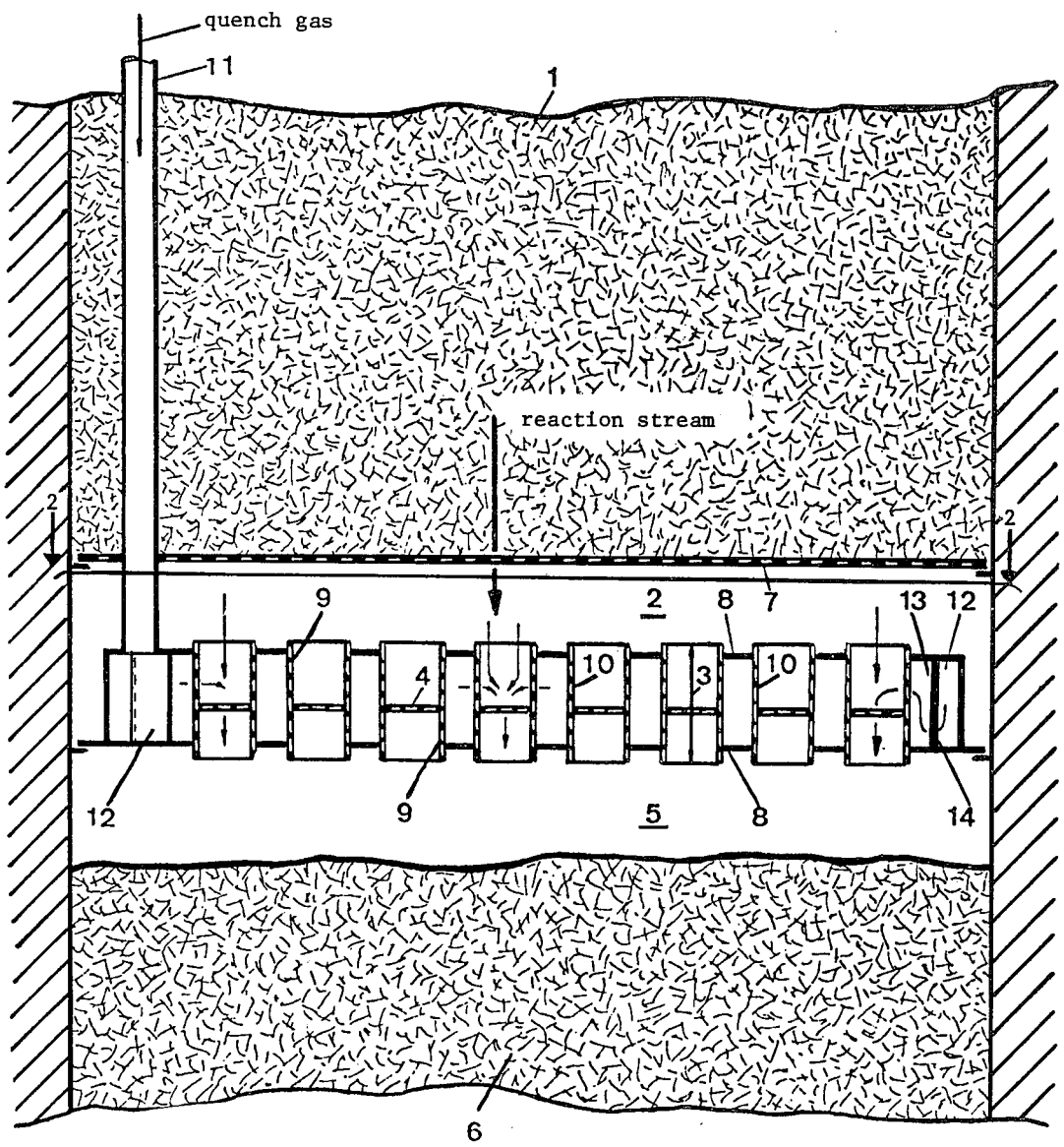
FIG. 1 is a vertical sectional view of the device according to this invention, for use in an ammonia synthesis converter, for example.
Figure 2:
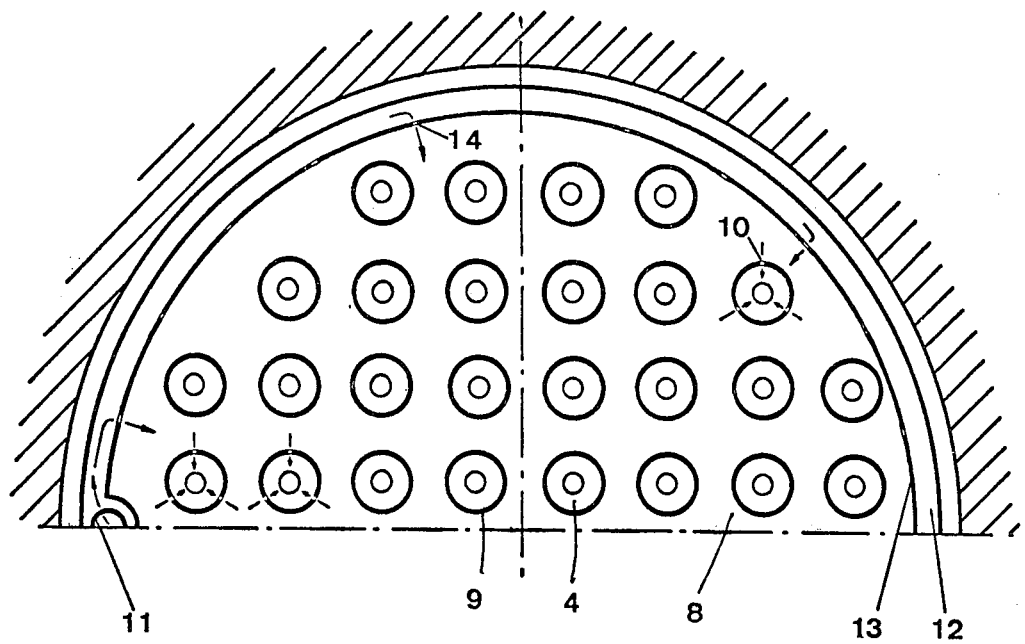
FIG. 2 is a cross sectional partial view on the line 2—2 of FIG. 1.

The main gas stream in FIG. 1 first passes across catalyst layer 1. Flow velocity is more or less uniform within the layer depending on grain size distribution and local density of the catalyst layer. Any differences in pressure and velocity will be equalized in equalizing space 2, which is a free space. The reaction gas stream passes from the equalizing space into a mixing path 3 in the form of tubes 9 where its flow velocity is increased owing to the reduced cross sectional area available as compared to that of the equalizing space. The tubes of the mixing path 3 are provided with restriction orifice plates 4, respectively, at approximately mid-level where another increase in flow velocity is imposed upon the gas stream.

The quench gas stream is admitted to the reaction gas stream ahead of restriction orifice plates 4 in the inlet half of the mixing path. The restriction orifice plates and the exit half of the mixing tubes interact to provide thorough mixing of the two gas streams. The gas mixture passes from the mixing path into a distribution space 5 from where it penetrates uniformly into the downstream catalyst layer 6.

The mechanical design of the mixing chamber may be described as comprising substantially a perforated support plate 7, two vertically spaced tube plates 8, and a plurality of laterally spaced vertically disposed rows of open ended mixing tubes 9. The mixing tubes 9 are sealed at their upper and lower end portions in the plates 8 providing closed areas about them for the flow of gas. A wall surrounds the plates 8 providing a space closed to the passage of reaction gas which can flow axially only through the mixing tubes 9. The mixing chamber is installed into a reaction vessel so as to provide a support for the superimposed catalyst layer 1. The outer side wall of the mixing chamber may be part of the reaction vessel or it may rest on a bracket attached to the vessel wall. The reaction gas passes from the catalyst layer 1 through the foraminous support plate 7 into the equalizing space 2.

If the gas flow across the catalyst layer 1 is irregular because of an irregular density of the dumped catalyst layer with consequent different exit temperatures at the outlet of the catalyst layer 1, a certain equalization of flow velocities and temperatures takes place in the equalizing space 2, the specific free volume of which is greater than that of the catalyst layer, particularly because of the accumulator effect produced in this space by the downstream restriction of the cross sectional area. For a given diameter of the reactor the free cross-sectional area for the gas stream in the open or equalizing space 2 is in any case larger than the free cross-sectional area at any point in catalyst bed 1. Should a non-uniform flow density occur in the catalyst bed due to a random disposition of the catalyst material, the flow density is then equalized or made uniform in equalizing space 2.

From the equalizing space 2, the gas penetrates into the various mixing tubes 9 without any substantial change in direction of flow. The inlet half of the mixing tubes 9 is provided with a restriction orifice plate or partition 4, which imposes an increase in flow velocity upon the gas. Through one or more openings 10 located in each tube 9 a short distance above the restriction orifice plate 4, the quench gas is admitted in a radial direction.

The thorough mixing of the two gas streams is attributable to the turbulence upstream and downstream of the restriction orifice plate 4, which takes place in the inlet half and the exit half of the mixing tubes 9. The quench gas stream, which is a stream of cold gas in this case, is admitted through a feed pipe 11 into an outer annular duct 12, which constitutes the enclosure of the mixing chamber. The inner limit of the annular duct is a sheet steel wall 13 with a series of spaced openings 14. The cold gas passes from this outer annular duct 12 through the openings 14 in a radial direction into the space around the mixing tubes 9 from where it penetrates uniformly through openings 10 into the mixing tubes. Each tube 9 has three openings 10 spaced equally from each other. The dual orifice effect of openings 14 and 10 causes a corresponding pressure drop for the quench gas and ensures a uniform distribution of the quench gas to the various mixing tubes. The orifice effect of the vertically spaced openings 14 and 10 and the effect of the mixing path with its restriction orifice plates 4 are harmonized to ensure that the mixing effect will be fully maintained at part load and overload operation. The homogeneous gas mixture leaves the mixing device in an axial direction and penetrates into the next catalyst layer where a uniform reaction is achieved owing to equal composition and temperature of the gas over the entire cross sectional area of the catalyst layer.

The following example reflects the data and flow velocities referring to a mixing chamber according to this invention.

EXAMPLE

Referring to an ammonia quench gas converter with a shell inside diameter $D_1 = 2,000$ mm and designed for a daily output of 1,000 tons $NH_3$, the first mixing chamber receives approximately 350,000 $Nm^3/hr$. of reaction gas from the first catalyst layer at 300 atm. abs. and 530°C. By admixing approximately 69,000 $Nm^3/hr$ quench gas at 50° – 100° C and 302 atm.abs., a homogeneous gas mixture of 452° C at the outlet of the mixing chamber shall be obtained. The mixing chamber is equipped with 174 mixing tubes 9 of 63 mm diameter. Gas flow velocity is 2.1 m/second at the inlet and 2.25 m/second at the outlet of the mixing tubes.

The aperture of each restriction orifice plate 4 installed in each mixing tube 9 has a diameter of 20 mm. Gas flow velocity across the restriction orifice plate is in the order of 22 m/second.

The outer annular duct 12 surrounding the mixing chamber and through which the quench gas is admitted, has a height of 180 mm and a width of 90 mm. From this annular duct, the quench gas passes through openings 14 of 6 mm diameter in a radial direction and at a velocity of about 10 m/second into the space around the mixing tubes.

The inlet half of each mixing tube is provided with three wall openings 10 of 3.8 mm diameter at 120° through which the quench gas penetrates in a radial direction at a flow velocity of approximately 15 m/second into the mixing tube where it mixes with the hot reaction gas.

The gas mixture leaving the mixing chamber and penetrating into the next catalyst layer 6 is fully homogeneous over the entire cross sectional area of the catalyst layer referring to both composition and temperature.

What We claim is:

1. The method of producing a homogenous gas mixture from two gas streams of different parameters, for multistage exothermic or endothermic reactions consisting of
   a. flowing a reaction gas stream through a catalyst layer to a relatively open space for equalizing the expansion and velocity of the reaction gas stream,
   b. the free cross-sectional area of the reaction gas stream in said open space being greater than the free cross-sectional area of the catalyst layer,
   c. causing the reaction gas stream in such space to pass concurrently through a plurality of parallel mixing zones,
   d. introducing quench gas through a two-stage pressure reduction to said mixing zones including first passing said quench gas to a closed area around said mixing zones and permitting expansion thereof to spaces around said zones so as to effect the first of said pressure reductions,
   e. causing quench gas to pass from the spaces around said zones into said zones so as to effect the second of said pressure reductions,
   f. passing the resultant reaction gas and quench gas mixture in parallel flow through restricted openings in said zones thereby increasing the velocity and effecting a complete homogenous mixture of the gases, and
   g. passing the homogenous gas mixture to the entrance of a second catalyst layer downstream.

* * * * *